(12) United States Patent
Mesher et al.

(10) Patent No.: US 8,871,693 B2
(45) Date of Patent: Oct. 28, 2014

(54) VOLATILE-PHOSPHORUS FREE GELLING AGENTS

(75) Inventors: Shaun T. Mesher, Calgary (CA); Chris Collett, Abdon (GB)

(73) Assignee: GasFrac Energy Services Inc., Calgary (CA)

( * ) Notice: Subject to any disclaimer, the term of this patent is extended or adjusted under 35 U.S.C. 154(b) by 573 days.

(21) Appl. No.: 13/057,275

(22) PCT Filed: Aug. 26, 2009

(86) PCT No.: PCT/CA2009/001159
§ 371 (c)(1),
(2), (4) Date: Feb. 2, 2011

(87) PCT Pub. No.: WO2010/022496
PCT Pub. Date: Mar. 4, 2010

(65) Prior Publication Data
US 2011/0143971 A1 Jun. 16, 2011

Related U.S. Application Data

(60) Provisional application No. 61/092,050, filed on Aug. 26, 2008.

(51) Int. Cl.
| | | |
|---|---|---|
| C09K 8/62 | (2006.01) | |
| C07F 9/22 | (2006.01) | |
| C07F 9/06 | (2006.01) | |
| C09K 8/64 | (2006.01) | |
| C07F 9/24 | (2006.01) | |
| C07F 9/165 | (2006.01) | |

(52) U.S. Cl.
CPC .............. *C07F 9/1651* (2013.01); *C09K 8/64* (2013.01); *C07F 9/222* (2013.01); *C07F 9/2416* (2013.01); *C07F 9/247* (2013.01); *C07F 9/2466* (2013.01); *C07F 9/2429* (2013.01); *C07F 9/2458* (2013.01); *C07F 9/242* (2013.01); *C07F 9/2408* (2013.01)
USPC ........... 507/236; 507/235; 507/263; 507/264; 562/8; 562/9; 562/10

(58) Field of Classification Search
None
See application file for complete search history.

(56) References Cited

U.S. PATENT DOCUMENTS

| 3,505,374 A | 4/1970 | Monroe | |
|---|---|---|---|
| 3,591,330 A * | 7/1971 | Redmore | ........................... 422/7 |

(Continued)

FOREIGN PATENT DOCUMENTS

| CA | 1 247 355 A | 12/1988 |
|---|---|---|
| CA | 2 514 140 A1 | 2/2006 |
| CA | 2552657 A1 | 7/2006 |

OTHER PUBLICATIONS

Crunden, E.W., and F.R. Hudson, "The Mechanism of Hydrolysis of Phosphorochloridates and Related Compounds. Part III. Phosphoramidochloridates," Journal of the Chemical Society, 1962, pp. 3591-3599.

(Continued)

*Primary Examiner* — John J Figueroa
(74) *Attorney, Agent, or Firm* — Christensen O'Connor Johnson Kindness PLLC

(57) ABSTRACT

A gelling agent for a hydrocarbon fracturing fluid is disclosed, comprising the general formula of: in which X is an $OR^1$, $NR^1R^2$, or $SR^1$ group, $R^1$ is an organic group having 2-24 carbon atoms, and $R^2$ is an organic group or a hydrogen. Y is an $NR^3R^4$ or $SR^3$ group, $R^3$ is an organic group having 2-24 carbon atoms, and $R^4$ is an organic group or a hydrogen. A method of making a gelling agent for a hydrocarbon fracturing fluid is also disclosed. Phosphorus oxyhalide is reacted with a chemical reagent to produce substantially only diester phosphorus oxyhalide, the chemical reagent comprising at least one of an organic alcohol having 2-24 carbon atoms, an organic amine with an organic group having 2-24 carbon atoms, and an organic sulfide having 2-24 carbon atoms. The diester phosphorus oxyhalide is then hydrolyzed to produce diester phosphoric acid.

29 Claims, 1 Drawing Sheet (3)

(56) References Cited

U.S. PATENT DOCUMENTS

| | | | |
|---|---|---|---|
| 3,757,864 | A | 9/1973 | Crawford |
| 3,816,620 | A | 6/1974 | Richter |
| 4,003,393 | A | 1/1977 | Jaggard |
| 4,034,023 | A | 7/1977 | Hardy, Sr. |
| 4,152,289 | A | 5/1979 | Griffin, Jr. |
| 4,153,649 | A | 5/1979 | Griffin, Jr. |
| 4,174,283 | A | 11/1979 | Griffin, Jr. |
| 4,200,540 | A | 4/1980 | Burnham |
| 4,316,810 | A | 2/1982 | Burnham |
| 4,622,155 | A | 11/1986 | Harris |
| 4,914,197 | A | 4/1990 | Yamamoto |
| 5,110,485 | A | 5/1992 | Huddleston |
| 5,260,051 | A | 11/1993 | Cho |
| 5,271,464 | A | 12/1993 | McCabe |
| 5,417,287 | A | 5/1995 | Smith |
| 5,505,936 | A | 4/1996 | Yano |
| 5,514,645 | A | 5/1996 | McCabe |
| 5,647,900 | A * | 7/1997 | Smith et al. .................. 106/285 |
| 5,863,415 | A * | 1/1999 | Zetlmeisl ........................ 208/47 |
| 5,872,272 | A | 2/1999 | Yano |
| 6,147,034 | A * | 11/2000 | Jones et al. .................... 507/238 |
| 6,149,693 | A * | 11/2000 | Geib ............................. 507/238 |
| 6,511,944 | B2 * | 1/2003 | Taylor et al. .................. 507/237 |
| 6,544,934 | B2 | 4/2003 | Taylor |
| 6,803,346 | B1 * | 10/2004 | Bailey et al. .................. 507/237 |
| 7,066,262 | B2 | 6/2006 | Funkhouser |
| 7,314,850 | B2 | 1/2008 | Taylor |
| 2005/0250652 | A1 * | 11/2005 | Taylor et al. .................. 507/203 |
| 2006/0037754 | A1 * | 2/2006 | Funkhouser ............... 166/308.1 |
| 2007/0032387 | A1 | 2/2007 | Delgado et al. |

OTHER PUBLICATIONS

Hochwalt, C.A., et al., "Alkyl Esters of Phosphoric Acid," Industrial and Engineering Chemistry, Jan. 1942, pp. 20-25.

International Search Report mailed Nov. 24, 2009, issued in corresponding International Application No. PCT/CA2009/001159, filed Aug. 26, 2009, 3 pages.

Moffatt, J.G., and H.G. Khorana, "Nucleoside Polyphosphates X. The synthesis and Some Reactions of Nucleoside-5-Phosphoromorpholidates and Related Compounds. Improved Methods for the Preparation of Nucleoside-5' Polyphosphates," Journal of the American Chemical Society 1961(83): 649-658, Feb. 1961.

"Phosphoryl Chloride," Wikipedia, The Free Encyclopedia, <http://en.wikipedia.org/wiki/Phosphoryl_chloride> [retrieved Jul. 9, 2008], 3 pages.

Stock, J.A., et al., "Amide as a Protecting Group in Phosphate Ester Synthesis. Part I. The Acid Hydrolysis of Some Phosphoramidic Diesters," Journal of the Chemical Society C, 1966, pp. 637-639.

Taylor, R.S., et al., "Prevention of Refinery Plugging by Residual Oil Gellant Chemicals in Crude-Optimization of Phosphonate Ester Oil Gellants," Journal of Canadian Petroleum Technology 44(5):16-20, May 2005.

Traylor, P.S., and F.H. Westheimer, "Mechanisms in the Hydrolysis of Phosphorodiamidic Chlorides," Journal of the American Chemical Society 87(3):553-559, Feb. 1965.

* cited by examiner

VOLATILE-PHOSPHORUS FREE GELLING AGENTS

TECHNICAL FIELD

Phosphorus-based gelling agents, gelling agents for liquefied petroleum gas, methods of preparing gelling agents, methods of treating subsurface formations.

BACKGROUND

Well production fluids containing traditionally produced dialkyl phosphoric acid ester gelling agents of the general formula:

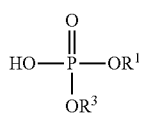

(where $R^1$ and $R^2$ are alkyl chains) have been found to contribute volatile phosphorus during refinery processing. This volatile phosphorus is a problem, since it condenses on the trays of distillation towers and causes plugging. Plugging leads to unexpected refinery shutdowns—events that can cost a refinery millions of dollars per day.

U.S. Pat. No. 7,066,262 has suggested two methods for dealing with this problem, both which are employed at the production stage. These methods include substituting another compound for the trialkyl phosphates during the manufacturing process or removing the trialkyl phosphates from the produced phosphoric acid esters.

SUMMARY

A gelling agent for a hydrocarbon fracturing fluid is disclosed, comprising the general formula of:

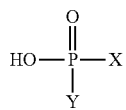

X is an $OR^1$, $NR^1R^2$, or $SR^1$ group, $R^1$ is an organic group having 2-24 carbon atoms, and $R^2$ is an organic group or a hydrogen. Y is an $NR^3R^4$ or $SR^3$ group, $R^3$ is an organic group having 2-24 carbon atoms, and $R^4$ is an organic group or a hydrogen.

A method of gelling a hydrocarbon fluid is also disclosed comprising adding the gelling agent to a hydrocarbon fluid to produce a gelled hydrocarbon fracturing fluid. In some embodiments, the hydrocarbon fluid comprises hydrocarbons having five or less carbons. In other embodiments, the hydrocarbon fluid excludes hydrocarbons having five or less carbons. A gelled hydrocarbon fracturing fluid is also disclosed comprising a hydrocarbon fluid gelled with the gelling agent. A method of treating a subterranean formation is also disclosed comprising the steps of introducing the gelled hydrocarbon fracturing fluid into the subterranean formation, and subjecting the gelled hydrocarbon fracturing fluid to pressures above the formation pressure. In some embodiments, the gelled hydrocarbon fracturing fluid is subjected to pressures at or above fracturing pressures.

A method of making a gelling agent for a hydrocarbon fracturing fluid is also disclosed. Phosphorus oxyhalide is reacted with a chemical reagent to produce substantially only diester phosphorus oxyhalide, the chemical reagent comprising at least one of an organic alcohol having 2-24 carbon atoms, an organic amine with an organic group having 2-24 carbon atoms, and an organic sulfide having 2-24 carbon atoms. The diester phosphorus oxyhalide is then hydrolyzed to produce diester phosphoric acid.

These and other aspects of the product and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Figure 1:
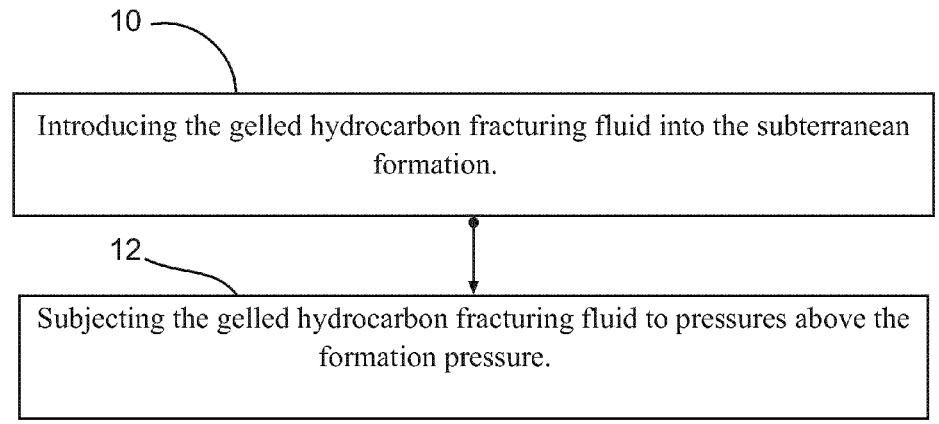
FIG. 1 is a flow diagram of a method of treating a subterranean formation.

Immaterial modifications may be made to the embodiments described here without departing from what is covered by the claims.

Although phosphoric acid based gelling agents and methods are highly successful in creating high-viscosity gelled liquid hydrocarbon treatment fluids, problems in downstream processes have been encountered as a result of the use of conventionally produced phosphorus-based gelling agents. For example, the plugging of refinery towers (which often process hydrocarbons produced from formations treated with gelled liquid hydrocarbon fracturing fluids) has caused many expensive, unplanned shut-downs of those towers. The plugging material has been found to be high in phosphorus and has historically been attributed to the phosphoric acid esters used as gelling agents in conventional reduced-volatility gelled liquid hydrocarbon treatment fluids used to stimulate the production of the hydrocarbons from a subterranean formation. The phosphoric acid esters have been thought to contribute volatile organic phosphorus, which may condense on distillation tower trays, resulting in the plugging of such trays, which may result in shut-downs of the towers. The volatile phosphorus also may carry over the tops of the distillation towers causing contamination of the hydrocarbon products produced. This volatile phosphorus problem has been attributed to the alleged inherent lack of stability of phosphate esters, which are believed to hydrolyze to form lower molecular weight compounds that are generally thought to cause the fouling problems. Despite these volatility and fouling problems, phosphoric acid ester gelling agents are desirable in that they carry a relatively low cost when compared to other hydrocarbon gelling agents.

When conventional phosphoric acid ester gelling agents are manufactured by traditional methods, they contain certain amounts of monoesters and diesters of orthophosphoric acids. The diesters are desirable, in that they are useful for gelling liquid hydrocarbons, whereas the monoesters are not useful for gelling liquid hydrocarbons and may be problematic. Conventionally produced phosphoric acid ester gelling agents may have little utility for gelling liquid hydrocarbons, if they have high monoester concentrations. Therefore, in order to counteract the potential problems presented by the monoesters, trialkyl phosphates (e.g., triethyl phosphate) have been included in conventional production methods to improve the yield of the diesters.

Residual trialkyl phosphates, such as triethyl phosphate, have been thought to be at least one of the sources of the volatility problems in downstream processing operations that are commonly associated with conventional phosphoric acid ester gelling agents (as opposed to the general wisdom that the volatility problems are associated with their alleged lack of stability). Residual trialkyl phosphates are problematic because of their low vapor pressure, which allows them to vaporize at the temperatures used in downstream processes, which can lead to fouling. Because most, if not all of the worldwide production of phosphoric acid ester gelling agents is done using processes that incorporate trialkyl phosphates, residual trialkyl phosphate contamination in the produced gelling agents is inevitable. The most common conventional method of production involves the reaction of phosphorus pentoxide with trialkyl phosphate and alcohol, which produces dialkyl orthophosphoric acid ester gelling agents.

Disclosed are gelling agents for a hydrocarbon fracturing fluid comprising the general formula of:

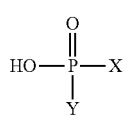

(2)

X being an $OR^1$, $NR^1R^2$, or $SR^1$ group, $R^1$ being an organic group having 2-24 carbon atoms, and $R^2$ being an organic group or a hydrogen. Y may be an $NR^3R^4$ or $SR^3$ group, $R^3$ an organic group having 2-24 carbon atoms, and $R^4$ an organic group or a hydrogen. Gelling agents of this variety are considered to be hardier and more resistant to decomposition under refinery conditions than traditionally produced dialkyl phosphoric acid ester gelling agents.

In some embodiments, $R^1$ has 2-12 carbon atoms. In further embodiments, such as the one indicated below as molecule (3), $R^1$ has 4-10 carbon atoms. Similarly, in some embodiments, $R^3$ has 2-12 carbon atoms, and in further embodiments such as molecule (3), $R^3$ has 4-10 carbon atoms. An example of such a gelling agent is disclosed below:

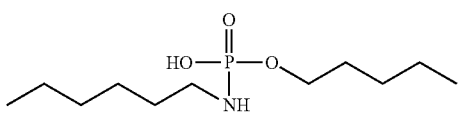

(3)

In molecule (3), the X group of (2) is now a C5 alkoxide group, and the Y group of (2) is now an NHC6 alkylamine group. As illustrated as an example in molecule (3), $R^1$ may be an alkyl group. As further illustrated as an example in molecule (3), $R^3$ may be an alkyl group.

In some embodiments, $R^2$ is an organic group with 2-12 carbon atoms. In further embodiments, such as the one indicated below as molecule (4), $R^2$ has 4-10 carbon atoms. An example of such a gelling agent is disclosed below:

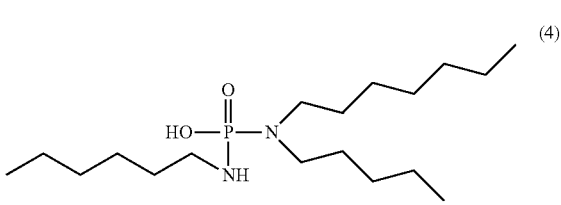 [SMILES: CCCCCCCN(CCCCC)P(=O)(O)NCCCCCC]

(4)

In molecule (4), the X group of (2) is now a dialkyl amine group with C5 and C7 alkyl side chains, and the Y group of (2) is now an NHC6 alkylamine group. As illustrated as an example in molecule (4), $R^2$ may be an alkyl group.

Similarly, in some embodiments, $R^4$ may be an organic group with 2-12 carbon atoms. In further embodiments, such as the one illustrated in molecule (5), $R^4$ has 4-10 carbon atoms. An example of such a gelling agent is disclosed below:

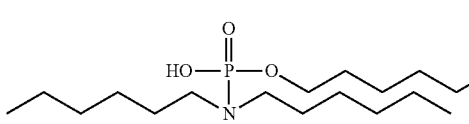

(5)

In molecule (5), the X group of (2) is now a C6 alkoxide group, and the Y group of (2) is now a dialkyl amine group with $R^3$ and $R^4$ as C6 alkyl side chains. As illustrated as an example in molecule (5), $R^4$ may be an alkyl group.

Any of the embodiments of gelling agents disclosed herein may be for a hydrocarbon fracturing fluid comprising hydrocarbons having five or less carbons. In some embodiments, the embodiments of gelling agents disclosed in the immediately preceding six paragraphs are for a hydrocarbon fracturing fluid comprising hydrocarbons having five or less carbons. Any of the gelling agents disclosed herein may be used to gel a hydrocarbon fluid to give a gelled hydrocarbon fracturing fluid. In some embodiments, a gelled hydrocarbon fracturing fluid may comprise a hydrocarbon fluid gelled with any of the gelling agents disclosed in the immediately preceding six paragraphs, the hydrocarbon fluid comprising hydrocarbons having five or less carbons. In further embodiments, the hydrocarbon fluid comprises liquefied petroleum gas. In other embodiments, the hydrocarbon fluid may be at least one of, for example, pentane, butane, propane, and ethane.

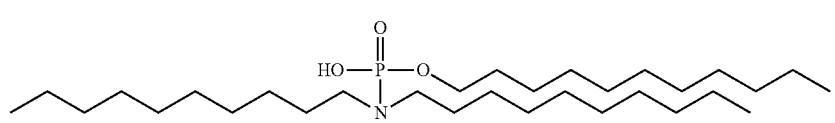

(6)

In some embodiments, $R^1$ has 6-24 carbon atoms. In further embodiments, such as the one indicated above as molecule (6), $R^1$ has 8-20 carbon atoms. Similarly, in some embodiments, $R^3$ has 6-24 carbon atoms, and in further embodiments such as molecule (6), $R^3$ has 8-20 carbon atoms. In some embodiments, $R^2$ is an organic group with 6-24 carbon atoms. In further embodiments, $R^2$ has 8-20 carbon atoms. Similarly, in some embodiments, $R^4$ may be an organic group with 6-24 carbon atoms. In further embodiments, such as the one illustrated above in molecule (6), $R^4$ has 8-20 carbon atoms.

Any of the embodiments of gelling agents disclosed herein may be for a hydrocarbon fracturing fluid comprising hydrocarbons excluding five or less carbons. In some embodiments, the embodiments of gelling agents disclosed in the immediately preceding paragraph are for a hydrocarbon fracturing fluid excluding hydrocarbons having five or less carbons. Due to the inherent danger and volatility of C5 and less hydrocarbons, frac operators working with longer hydrocarbon chain fluids generally prefer not to have any C5 or less compounds present in their hydrocarbon fracturing fluids. Any of the gelling agents disclosed herein may be used to gel a hydrocarbon fluid to give a gelled hydrocarbon fracturing fluid. In some embodiments, a gelled hydrocarbon fracturing fluid may comprise a hydrocarbon fluid gelled with any of the gelling agents disclosed in the immediately preceding paragraph, the hydrocarbon fluid excluding hydrocarbons having five or less carbons. Excluding, in this document, is understood to mean that hydrocarbons of five or less carbons are present in less than 5%, and in some embodiments, less than 1%, concentration in the hydrocarbon fracturing fluid being used.

In other embodiments, at least one of $R^1$, $R^2$, $R^3$, and $R^4$ may be at least one of a phenyl, aryl, alkenyl, alkynyl, cyclo, and ether group. In other embodiments, other suitable organic groups may be used. Examples of such gelling agents are disclosed below:

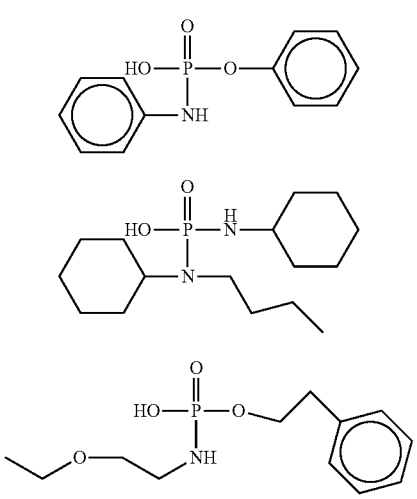

In molecule (7), the X group of (2) is a benzyl alkoxide group, and the Y group of (2) is a benzyl amine group. In molecule (8), the X group of (2) is a cyclohexyl amine group, and the Y group of (2) is a cyclohexyl amine group with a C4 alkyl side chain. In molecule (9), the X group of (2) is now a (2-benzyl)ethyl alkoxide group, and the Y group of (2) is now an ethoxyethane substituted amine group.

In some embodiments, such as the one illustrated above in molecules (3) and (5), the X group of (2) is an $OR^1$ group and Y group of (2) is an $NR^3R^4$ group. In other embodiments, such as the ones illustrated in (4) and (8), the X group of (2) is an $NR^1R^2$ group and the Y group of (2) is an $NR^3R^4$ group.

In some embodiments, such as the one illustrated below in molecule (10), the X group of (2) is an $OR^1$ group and the Y group of (2) is an $SR^3$ group.

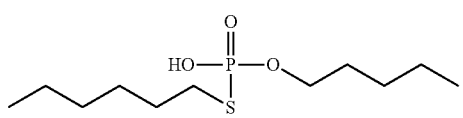

In some embodiments, such as the one illustrated below in molecule (11), the X group of (2) is an $NR^1R^2$ group and the Y group of (2) is an $SR^3$ group.

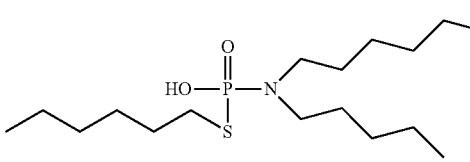

In some embodiments, such as the one illustrated below in molecule (12), the X group of (2) is an $SR^1$ group and the Y group of (2) is an $SR^3$ group.

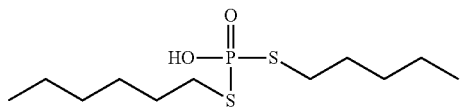

Any of the gelling agents disclosed herein may be used to gel a hydrocarbon fluid to give a gelled hydrocarbon fracturing fluid. It should be understood that various other species, such as activators and/or breakers may be necessarily added, introduced, or present in order to induce gellation of the hydrocarbon fluid. In addition, further species may be required, such as proppant, as well as other gelling agents to complete the gelled hydrocarbon fracturing fluid.

Exemplary activators include, but are not limited to: ferric salt (such as ferric sulfate or ferric chloride), alkali metal aluminate (such as sodium aluminate), basic aluminum or iron compounds, aluminum isopropoxide, hydrated alumina, or any such suitable polyvalent metal ions including aluminum ions, gallium ions, lanthanum ions, ruthenium ions, iron ions, or lanthanide rare earth series ions. The polyvalent metal ions may have a +3 oxidation state. A ferric iron salt may typically be mixed with amines, surfactants and water to form a liquid activator composition. An example of a commercially available ferric iron activator composition is "EA-3™" sold by Ethox Chemicals, Inc. of Greenville, S.C. Suitable activator compositions also may comprise amines, surfactants, water, or other suitable components.

Any breaker present may be so in an amount sufficient to reduce the viscosity of the gelled liquid hydrocarbon fracturing fluid at the desired time. The breaker may be at least one of, for example, hard burned magnesium oxide, an alkali metal carbonate, alkali metal bicarbonate, alkali metal acetate, an alkaline earth metal oxides, an alkali metal hydroxide, an amine, a weak acid, and a reducing agent capable of reducing ferric iron to ferrous iron.

In some embodiments, the hydrocarbon fracturing fluid comprises at least one fluid having between 6 and 24, or 8 and 20 carbon atoms, for example diesel or crude oil. In other embodiments, the hydrocarbon fluid comprises liquefied petroleum gas. In further embodiments, the organic groups of X and Y are commensurate in length with the hydrocarbon fracturing fluid. For example, if an LPG mix containing butane and propane is used as a hydrocarbon fluid, then a suitable gelling agent may have the formula of molecule (13) below:

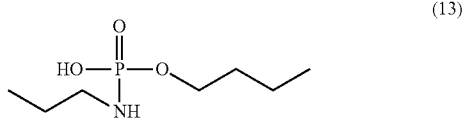

(13)

In molecule (13), the $R^1$ group is a butyl group, and the $R^3$ group is a propyl group. In other embodiments, other lengths of side chains may be used. In general, commensurate means corresponding in size, shape, degree or extent. Thus, commensurate in length refers to the fact that the side chains may be corresponding in size or length with the hydrocarbon fluid. Thus, this could mean that the side chains in (13) may be, for example, C5 side chains, with the hydrocarbon fracturing fluid being propane. In other embodiments, the side chains may have C8 side chains, with the hydrocarbon fracturing fluid being a C8-10 hydrocarbon fluid. In some embodiments, commensurate in length means the organic groups have a carbon length within 2 or 3 carbons of the length of the hydrocarbon fracturing fluid. In other embodiments, commensurate in length means the organic groups have a carbon length within 7 carbons of the length of the hydrocarbon fracturing fluid.

In other embodiments, the organic groups of X and Y may be commensurate in shape with the hydrocarbon fracturing fluid. An example of such a gelled hydrocarbon fracturing fluid includes an aromatic hydrocarbon fluid (for example toluene) and a gelling agent with at least one aromatic sidechain (for example molecule (7)). In these embodiments, the R sidechains correspond with the nature of the solvent used. Reference to the organic groups refers to at least one of any organic groups present.

Referring to FIG. 1, a method of treating a subterranean formation is illustrated. In step 10, a gelled hydrocarbon fracturing fluid (as disclosed herein) is introduced into the subterranean formation. In step 12, the gelled hydrocarbon fracturing fluid is subjected to pressures above the formation pressure. In some embodiments, the gelled hydrocarbon fracturing fluid is subjected to pressures at or above fracturing pressures. Fracturing techniques are well known, and need not be explained in detail here.

Figure 2:
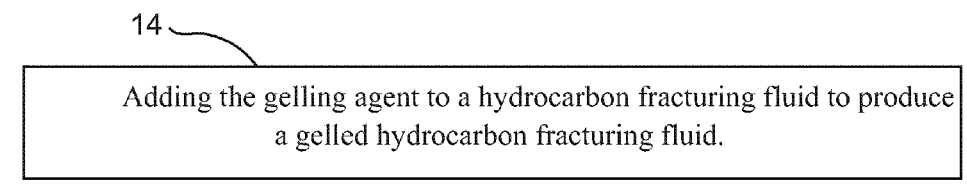
FIG. 2 is a flow diagram of a method of gelling a hydrocarbon fluid.

Referring to FIG. 2, a method of gelling a hydrocarbon fluid is illustrated. In step 14, any of the gelling agents disclosed herein are added to a hydrocarbon fracturing fluid to produce a gelled hydrocarbon fracturing fluid. In some embodiments, the hydrocarbon fluid comprises hydrocarbons having five or less carbons. In some embodiments, the hydrocarbon fluid excludes hydrocarbons having five or less carbons. As indicated above, it is understood that other chemicals, such as a source of polyvalent metal ions, may be necessary to induce gellation of the hydrocarbon fracturing fluid.

Figure 3:
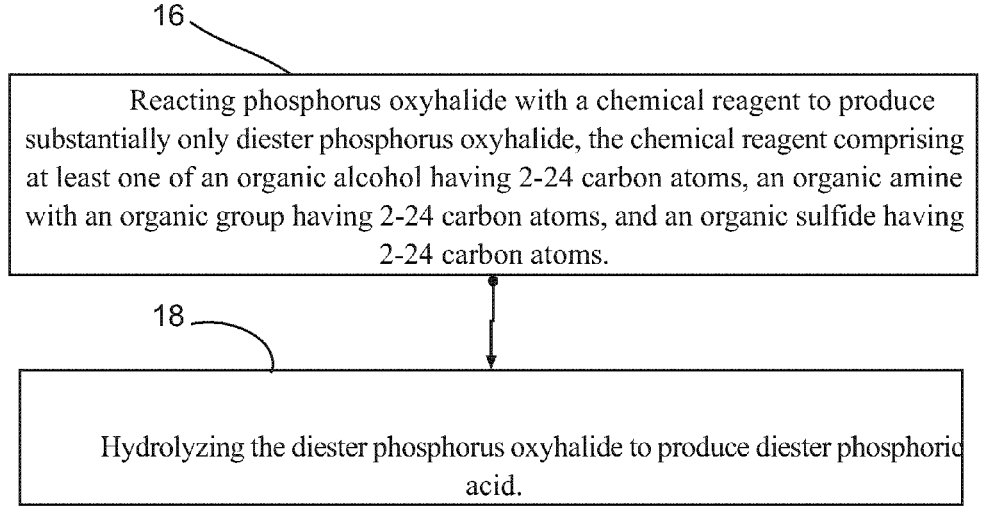
FIG. 3 is a flow diagram of a method of making a gelling agent for a hydrocarbon fracturing fluid.

Referring to FIG. 3, a method of making a gelling agent for a hydrocarbon fracturing fluid is illustrated. In step 16, phosphorus oxyhalide is reacted with a chemical reagent to produce substantially only diester phosphorus oxyhalide. Phosphorus oxyhalide may include at least one of the oxychloride, oxybromide, oxyflouride, or oxyiodide forms, for example. Substantially only refers to the fact that, of the phosphate ester products produced, at least 90% (for example at least 95% or 98%), is the diester form. In other embodiments, substantially only refers to at least 80% (for example at least 85%) of the phosphate ester products being of the diester form. This will result in the production of substantially pure gelling agents. The chemical reagent comprises at least one of an organic alcohol having 2-24 carbon atoms, an organic amine with an organic group having 2-24 carbon atoms, and an organic sulfide having 2-24 carbon atoms. Diester is not intended here to be limiting to oxygen atoms only bonding to the phosphorus atom, but includes sulfur and nitrogen atoms as well. For example, diester can refer to diamide, disulfide, and monoester-monoamide products. By producing substantially only the diester form, only a negligible or non-existent portion of mono-ester gelling agent is produced in step 18. This is desirable, as the mono-ester products are generally useless as gelling agents, and are thought to contribute to volatile phosphate production in refinery processing. In step 18, the diester phosphorus oxyhalide is hydrolyzed to produce diester phosphoric acid. The diester phosphoric acid produced in this step is the gelling agent, and includes any of the gelling agents disclosed herein. The phosphorus oxyhalide may be reacted in solution or without solvent.

In some embodiments, reacting in step 16 further comprises controlling the introduction of the chemical reagent (for example adding the chemical reagent dropwise) into the phosphorus oxyhalide. By controlling the introduction of the chemical reagent into the phosphorus oxyhalide, the yield of diester product is enhanced. This is likely due to the fact that, prior to the formation of any diester, all of the phosphorus present has reacted to form mono-ester products. The mono-ester products are then further reacted to completion to form the diester form. Controlling the addition may include slowly adding. In some embodiments, the chemical reagent is introduced in a diluted form. In some embodiments, reacting further comprises reacting at temperatures below room temperature. In some embodiments, reacting further comprises adding a base, such as pyridine or triethylamine for example. By employing the phosphorus oxyhalide reaction disclosed above, no trialkyl phosphates will be present in the gelling agent, the resulting hydrocarbon fracturing fluids, and any subsequently produced well fluids.

In some embodiments, the chemical reagent comprises the organic alcohol. In further embodiments, the organic alcohol has 2-12 carbon atoms. In other embodiments, the organic alcohol has 6-24 carbon atoms. Examples of gelling agents produced with the method in which the chemical reagent comprises organic alcohol are illustrated by molecules 3 and 5. The organic alcohol may have the general formula $OR^1$, $R^1$ being an organic group. In other embodiments, the chemical reagent comprises the organic amine. Examples of gelling agents produced with the method in which the chemical reagent comprises organic amines are illustrated by molecules 3 and 4. As illustrated above, the organic amine may have the general formula of $NR^1R^2$, $R^1$ being an organic group having 2-24 carbon atoms, and $R^2$ being an organic group or a hydrogen as above. In some embodiments, $R^1$ of the organic amine has 2-12 carbon atoms. In other embodiments, $R^1$ of the organic alcohol has 6-24 carbon atoms. In some embodiments, $R^2$ of the organic amine has 2-12 carbon atoms. In some embodiments, $R^2$ of the organic amine has 6-24 carbon atoms. In further embodiments, the chemical reagent comprises the organic sulfide. In some embodiments, the organic sulfide has 2-12 carbon atoms. In other embodiments, the organic sulfide has 6-24 carbon atoms. Examples of gelling agents produced with the method in which the chemical reagent comprises organic sulfides are illustrated by molecules 9 and 10. The organic sulfide may have the general formula of $SR^1$, $R^1$ being an organic group.

In some embodiments, the chemical reagent comprises a first compound comprising an organic alcohol having 2-24 carbon atoms, an organic amine with an organic group having 2-24 carbon atoms, or an organic sulfide having 2-24 carbon atoms, and a second compound comprising an organic alcohol having 2-24 carbon atoms, an organic amine with an organic group having 2-24 carbon atoms, or an organic sulfide having 2-24 carbon atoms. In this embodiment, reacting may further comprise reacting the phosphorus oxyhalide with the first compound to produce substantially only monoester phosphorus oxyhalide, and reacting the monoester phosphorus oxyhalide with the second compound to produce substantially only diester phosphorus oxyhalide. An example of this type of method is illustrated below in example 2. This method may be used to produce any gelling agent with different groups attached to the phosphorus atom.

Examples of Gelling Agent Synthesis.
1. Diamide Synthesis Method.

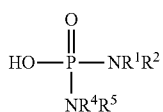

A 500 mL 3 necked round bottomed flask was fitted with a septum, stir bar and nitrogen supply. The flask was flushed with nitrogen (3 psi), which was vented to an oil bubbler. The flask was then cooled to −60° C. using a dry ice/acetone bath and flushed with nitrogen. POCl$_3$ (100 mmol) and dichloromethane (300 mL) were added to the flask and allowed to cool. A solution of the amine, for example hexylamine, (400 mmol) in dichloromethane (100 mL) was added to the flask dropwise over two hours using an addition funnel. Once addition was complete, the dry ice/acetone bath was removed and the solution was stirred for one hour at room temperature. The solution was then cooled to 0° C. and the amine hydrochloride salt was extracted using ice water. The dichloromethane phase was dried over anhydrous magnesium sulphate. Diethyl ether was then added to induce crystallization. The white solid obtained was filtered and re-crystallized from dichloromethane/ether to yield the phosphorodiamidic chloride. To produce the final diamidic acid product, the phosphorodiamidic chloride was dissolved in a 50/50 blend of acetone and water. The phosphorodiamidic chloride was initially insoluble but dissolved upon heating. The solution was refluxed for two hours, during which a white solid precipitated out. The acetone was removed by rotary evaporation and the solid was filtered and dried to yield the phosphorodiamidic acid product.

2. Mixed Amide and Ester Synthesis.

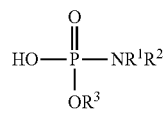

A 500 mL 3 necked round bottomed flask was fitted with a septum, stir bar and nitrogen supply. The flask was flushed with nitrogen (3 psi), which was vented to an oil bubbler. The flask was cooled to −60° C. using a dry ice/acetone bath and flushed with nitrogen. POCl$_3$ (100 mmol) and dichloromethane (300 mL) were added to the flask and allowed to cool. A solution of the alcohol (100 mmol) in dichloromethane (50 mL) was added to the flask dropwise using an addition funnel. Once addition was complete, the dry ice/acetone bath was removed and the solution was stirred for one hour at room temperature. The solution was then cooled back down to −60° C. and a solution of the amine (200 mmol) in dichloromethane (50 mL) was added to the flask dropwise using an addition funnel. Once addition was complete, the bath was removed and the solution was stirred for one hour at room temperature. The amine hydrochloride salt was then extracted using ice water. The dichloromethane phase was dried over anhydrous magnesium sulphate. Diethyl ether was then added to induce crystallization, of the N,N,O-alkylphosphoroamidic chloride ester product. To produce the final product, the chloride ester product was dissolved in a 50/50 blend of acetone and water and was refluxed for two hours. The acetone was removed by rotary evaporation and the solid was filtered and dried to yield the N,N,O-alkylphosphoroamidic acid ester product.

3. C5—Diester (Pentanol)

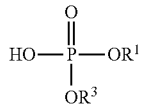

Synthesis Method. Fit a 500 ml 4 necked round bottomed flask with a septum, stir bar, thermometer and nitrogen supply. Flush the flask with nitrogen (3 psi), which is vented to an oil bubbler. Cool the flask to −20° C. using dry ice and flush with nitrogen. Add POCl$_3$ (9.1 ml, 100 mmol) and ether (250 ml). Add a solution of pentanol (200 mmol, 17.63 g, 21.74 ml) and pyridine (15.82 g, 16.175 ml, 200 mmol) to the flask dropwise over one hour using an addition funnel. Once addition is complete, remove the bath and warm to RT (still under nitrogen). Stir for 2 additional hours. After this, filter the solution to collect the white pyridinium hydrochloride salt (save and weigh). For the hydrolysis: Put the filtrate into a new flask (500 ml). Add water (10 mls, 555 mmol) and acetone 150 mls and stir for 1 hour at room temperature. Rotovap the acetone off (no heat) and separate the remaining liquid with ether in a sep funnel and add ~100 ml of DI water. Wash the ether layer a further two times with water. Then dry the ether layer over anhydrous magnesium sulphate. Rotavap the ether to give the final product. Record acid number. The product is dipentyl-phosphate diester.

4. C6—Diester (1-hexanthiol)

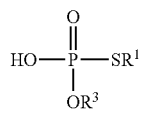

Synthesis Method. Fit a 500 ml 4 necked round bottomed flask with a septum, stir bar, thermometer and nitrogen supply. Flush the flask with nitrogen (3 psi), which is vented to an oil bubbler. Cool the flask to −20° C. using dry ice and flush with nitrogen. Add $POCl_3$ (9.1 ml, 100 mmol) and ether (250 ml). Add a solution of hexanethiol (200 mmol, 23.65 g, 28.22 ml) and pyridine (15.82 g, 16.175 ml, 200 mmol) to the flask dropwise over one hour using an addition funnel. Once addition is complete, remove the bath and warm to RT (still under nitrogen). Stir for 2 additional hours. After this, filter the solution to collect the white pyridinium hydrochloride salt (save and weigh). For the hydrolysis: Put the filtrate into a new flask (500 ml). Add water (10 mls, 555 mmol) and acetone 150 mls and stir for 1 hour at room temperature. Rotavap the acetone off (no heat) and separate the remaining liquid with ether in a sep funnel and add ~100 ml of DI water. Wash the ether layer a further two times with water. Then dry the ether layer over anhydrous magnesium sulphate. Rotavap the ether to give the final product. Record acid number. Product is dihexyl-thiophosphate diester.

5. C6—Diester (alcohol/amine)

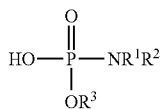

Synthesis Method. Fit a 500 ml 4 necked round bottomed flask with a septum, stir bar, thermometer and nitrogen supply. Flush the flask with nitrogen (3 psi), which is vented to an oil bubbler. Cool the flask to −20° C. using dry ice and flush with nitrogen. Add $POCl_3$ (9.1 ml, 100 mmol) and ether (250 ml). Add a solution of alcohol, for example hexanol, (100 mmol, 8.82 g, 10.87 ml), amine, for example hexylamine, (100 mmol, 10.12 g, 13.21 mls) and pyridine (15.82 g, 16.175 ml, 200 mmol) to the flask dropwise over one hour using an addition funnel. Once addition is complete, remove the bath and warm to room temperature (still under nitrogen). Stir for 2 additional hours. After this, filter the solution to collect the white pyridinium hydrochloride salt (save and weigh). For the hydrolysis: Put the filtrate into a new flask (500 ml). Add water (10 mls, 555 mmol) and acetone 150 mls and stir for 1 hour at reflux. Rotavap the acetone off (no heat) and separate the remaining liquid with ether in a sep funnel and add ~100 ml of de-ionized water. Wash the ether layer a further two times with water. Then dry the ether layer over anhydrous magnesium sulphate. Rotavap the ether to give the final product. Record acid number. Product is dipentyl-phosphate diester.

$R^1$, $R^2$, $R^3$, and $R^4$ are understood as referring to the same groups throughout this document. It should be understood that at least two of the R groups may be the same group on one gelling agent molecule. Organic groups may refer to any group with at least one carbon atom, as long the resulting gelling agent is suitable for its purpose.

The methods disclosed herein produce substantially pure gelling agents that do not pose a volatile phosphorus problem in downstream processes. Further, by following the methods disclosed herein, gelling agents may be produced that form no volatile organic phosphorus at all. Thus, these gelling agents are highly desirable, in that they avoid the problems described above associated with volatile phosphorus.

Hydrocarbons are understood to include molecules with hydrogen bonded to carbon. This may include compounds with other atoms, such as oxygen or nitrogen, for example, and is not restricted to conventional compounds that contain only carbon and hydrogen.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A gelling agent for a hydrocarbon fracturing fluid comprising the general formula of:

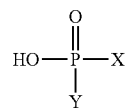

X being an $OR^1$ group, $R^1$ being an organic group having 2-24 carbon atoms; and Y being an $NR^3R^4$ group, $R^3$ being an organic group having 2-24 carbon atoms, and $R^4$ being an organic group or a hydrogen.

2. The gelling agent of claim 1 in which $R^1$ is an alkyl group.

3. The gelling agent of claim 1 in which $R^1$ comprises at least one of a phenyl, aryl, alkenyl, alkynyl, cyclo, and ether group.

4. The gelling agent of claim 1 in which $R^3$ is an alkyl group.

5. The gelling agent of claim 1 in which $R^3$ comprises at least one of a phenyl, aryl, alkenyl, alkynyl, cyclo, and ether group.

6. The gelling agent of claim 1 in which $R^4$ is an alkyl group.

7. The gelling agent of claim 1 in which $R^4$ comprises at least one of a phenyl, aryl, alkenyl, alkynyl, cyclo, and ether group.

8. The gelling agent of claim 1 in which the gelling agent is substantially pure.

9. The gelling agent of claim 1 in which $R^1$ has 2-12 carbon atoms.

10. The gelling agent of claim 9 in which $R^1$ has 4-10 carbon atoms.

11. The gelling agent of claim 1 in which $R^3$ has 2-12 carbon atoms.

12. The gelling agent of claim 11 in which $R^3$ has 4-10 carbon atoms.

13. The gelling agent of claim 1 in which $R^4$ has 2-12 carbon atoms.

14. The gelling agent of claim 13 in which $R^4$ has 4-10 carbon atoms.

15. The gelling agent of claim 1 being for a hydrocarbon fracturing fluid comprising hydrocarbons having five or fewer carbons.

16. The gelling agent of claim 1 being for a hydrocarbon fracturing fluid excluding hydrocarbons having five or fewer carbons.

17. The gelling agent of claim 1 in which $R^1$ has 6-24 carbon atoms.

18. The gelling agent of claim 17 in which $R^1$ has 8-20 carbon atoms.

19. The gelling agent claim 1 in which $R^3$ has 6-24 carbon atoms.

20. The gelling agent of claim 19 in which $R^3$ has 8-20 carbon atoms.

21. The gelling agent of claim 1 in which $R^4$ is an organic group with 6-24 carbon atoms.

22. The gelling agent of claim 21 in which $R^4$ has 8-20 carbon atoms.

23. A gelled hydrocarbon fracturing fluid comprising a hydrocarbon fluid gelled with the gelling agent of claim 1.

24. A gelled hydrocarbon fracturing fluid comprising a hydrocarbon fluid gelled with the gelling agent of claim 9, the hydrocarbon fluid comprising hydrocarbons having five or fewer carbons.

25. The gelled hydrocarbon fracturing fluid of claim 24 in which the hydrocarbon fluid comprises liquefied petroleum gas.

26. A gelled hydrocarbon fracturing fluid comprising a hydrocarbon fluid gelled with the gelling agent of claim 16 the hydrocarbon fluid excluding hydrocarbons having five or fewer carbons.

27. The gelled hydrocarbon fracturing fluid of claim 23 further comprising at least one of an activator and a breaker.

28. A method of treating a subterranean formation comprising the steps of:
 introducing the gelled hydrocarbon fracturing fluid of claim 23 into the subterranean formation; and
 subjecting the gelled hydrocarbon fracturing fluid to pressures above the formation pressure.

29. The method of claim 28 in which the gelled hydrocarbon fracturing fluid is subjected to pressures at or above fracturing pressures.

* * * * *